Figure 1:
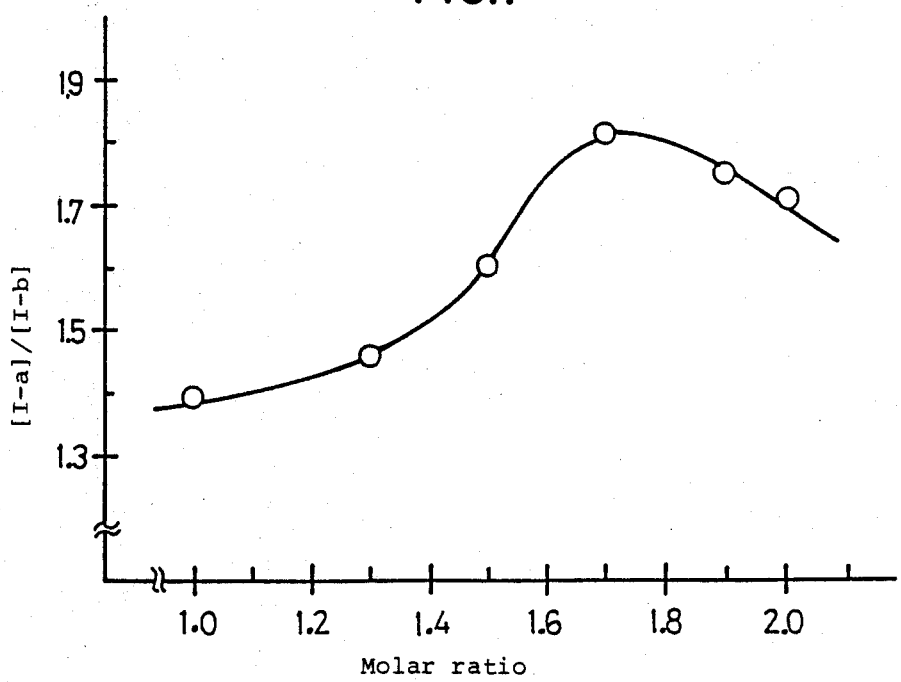

United States Patent [19]

Minai et al.

[11] Patent Number: 4,714,782
[45] Date of Patent: Dec. 22, 1987

[54] PROCESS FOR PREPARING OPTICALLY ACTIVE 4-HYDROXY-2-CYCLOPENTENONES

[75] Inventors: Masayoshi Minai, Moriyama; Yuji Ueda, Izumi, both of Japan

[73] Assignee: Sumitomo Chemical Co., Ltd., Osaka, Japan

[21] Appl. No.: 700,890

[22] Filed: Feb. 12, 1985

[30] Foreign Application Priority Data

Feb. 14, 1984 [JP] Japan .................. 59-026647
Mar. 23, 1984 [JP] Japan .................. 59-056987

[51] Int. Cl.⁴ ............................................. C07C 45/78
[52] U.S. Cl. ..................................... 568/347; 549/302
[58] Field of Search ...................... 568/347; 549/302

[56] References Cited

U.S. PATENT DOCUMENTS 4,367,340 1/1983 Rickards et al. ............... 568/347
4,487,957 12/1984 Martel et al. ................... 549/302

FOREIGN PATENT DOCUMENTS 23454 2/1981 European Pat. Off. ......... 549/309
58491 8/1982 European Pat. Off. ......... 549/309
159777 10/1982 Japan ................................ 549/302
44836 3/1983 Japan ................................ 549/302

Primary Examiner—James H. Reamer
Attorney, Agent, or Firm—Birch, Stewart, Kolasch and Birch

[57] ABSTRACT

A process for preparing an optically active 2-substituted or unsubstituted-4-hydroxy-2-cyclopentenone of the formula:

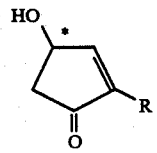

wherein R is a hydrogen atom, an allyl group or a propargyl group, which comprises reacting the corresponding 2-substituted or unsubstituted-4-hydroxy-2-cyclopentenone of the formula:

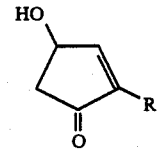

wherein R is defined above with a lactone chosen from (1R,5S)-6,6-dimethyl-4-hydroxy-3-oxabicyclo[3.1.0-]hexan-2-one or (1S,5R)-6,6-dimethyl-4-hydroxy-3-oxabicyclo[3.1.0]hexan-2-one in a molar ratio of 1.5 - 2:1 in the presence of p-toluenesulfonic acid or benzenesulfonic acid in the coexistence of an organic solvent under elimination of water as an azeotropic mixture with the organic solvent to obtain a reaction mixture comprising (1R,5S)-6,6-dimethyl-3-oxa-4(R)-[1(R)-4-oxo-2-substituted or unsubstituted-2-cyclopentenyloxy]bicyclo[3.1.0]hexan-2-one or (1S,5R)-6,6-dimethyl-3-oxa-4(S)-[1(S)-4-oxo-2-substituted or unsubstituted-2-cyclopentenyloxy]bicyclo[3.1.0]hexan-2-one of the formula:

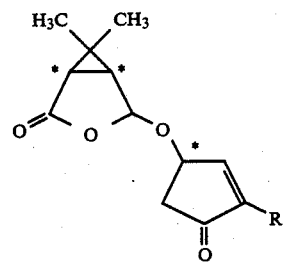

wherein R is as defined above, of which either one isomer is contained in a considerably larger amount than the other isomer, separating the isomer having the larger content from the reaction mixture and hydrolyzing the separated isomer to give the optically active 2-substituted or unsubstituted-4-hydroxy-2-cyclopentenone.

13 Claims, 1 Drawing Figure

PROCESS FOR PREPARING OPTICALLY ACTIVE 4-HYDROXY-2-CYCLOPENTENONES

The present invention relates to a process for preparing optically active 4-hydroxy-2-cyclopentenones. More particularly, it relates to an improved process for preparing optically active 2-substituted or unsubstituted-hydroxy-4-hydroxy-2-cyclopentenones of the formula:

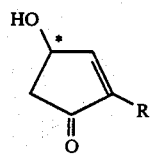
(I)

wherein R is a hydrogen atom, an allyl group or a propargyl group.

Said optically active 2-substituted or unsubstituted)-4-hydroxy-2-cyclopentenones (I) are known to be intermediates in the synthesis of pharmaceuticals and agrochemicals. For instance, 4(R)-hydroxy-2-cyclopentenone is widely used as the starting material for production of prostaglandins such as PGE$_2$ and PGF$_{2\alpha}$. Further, for instance, 4(R)-hydroxy-2-allyl or propargyl-2-cyclopentenone can be used as an intermediate in the synthesis of known or novel prostaglandins.

For production of the optically active 2-substituted or unsubstituted-4-hydroxy-2-cyclopentenones (I), there have been known various processes. For instance, Japanese patent publication (unexamined) Nos. 159777/1982 and 41836/1983 disclose respectively the process for preparing optically active 4-hydroxy-2-cyclopentenone and the process for preparing optically active 2-allyl-4-hydroxy-2-cyclopentenone. The former process comprises reacting 4-hydroxy-2-cyclopentenone with a lactone in a molar ratio of 1.2 - 1.3:1, separating one of the optically active cyclopentenone ethers from the reaction mixture and hydrolyzing the separated optically active cyclopentenone ether. However, said literature is entirely silent on the proportion of the optically active cyclopentenone ethers in the reaction mixture. When, for instance, (1R,5S)-6,6-dimethyl-4-hydroxy-3-oxabicyclo[3.1.0]hexan-2-one is used as the lactone, there is obtained a reaction mixture comprising (1R,5S)-6,6-dimethyl-3-oxa-4(R)-[1(R)-4-oxo-2-cyclopentenyloxy]bicyclo[3.1.0]hexan-2-one and (1R,5S)-6,6-dimethyl-3-oxa-4(R)-[1(S)-4-oxo-2-cyclopentenyloxy]bicyclo[3.1.0]hexan-2-one, but the proportion or contents of these cyclopentenone ethers in the reaction mixture are not clarified. Judging from the working example wherein the reaction mixture is subjected to separation by column chromatography, the proportion of the cyclopentenone ethers may be close to 1.

The latter process comprises reacting 2-allyl-4-hydroxy-2-cyclopentenone with a lactone in a molar ratio of 1:1, separating one of the optically active cyclopentenone ethers from the reaction mixture and hydrolyzing the separated optically active cyclopentenone ether. However, said literature is also silent on the proportion of the optically active cyclopentenone ethers in the reaction mixture. When, for instance, (1R,5S)-6,6-dimethyl-4-hydroxy-3-oxabicyclo[3.1.0]hexan-2-one is used as the lactone, there is obtained a reaction mixture comprising (1R,5S)-6,6-dimethyl-3-oxa-4(R)-[1(R)-4-oxo-3-allyl-2-cyclopentenyloxy]bicyclo[3.1.0]hexan-2-one and (1R,5S)-6,6-dimethyl-3-oxa-4(R)-[1(S)-4-oxo-3-allyl-2-cyclopentenyloxy]bicyclo[3.1.0]hexan-2-one, but the proportion or contents of these cyclopentenone ethers in the reaction mixture is not stated. Judging from the working example wherein the reaction mixture is subjected to separation by column chromatography, the proportion, of the cyclopentenone ethers may be close to 1.

As understood from the above, the reaction between the starting 2-substituted or unsubstituted-4-hydroxy-2-cyclopentenone and the lactone in the conventional processes gives the optically active isomers only in a proportion close to 1. Because of this, the recovery of the optically active isomers in good yields is not possible. Further, the isolation and purification of the optically active isomers are difficult.

It has now been unexpectedly found that when the reaction of the starting 2-substituted or unsubstituted-4-hydroxy-2-cyclopentenone with the lactone is carried out using them in a certain molar ratio in the presence of a certain specific catalyst, there is obtained a reaction mixture comprising the optically active cyclopentenone ethers wherein the proportion of them is considerably apart from 1 or the content of either one of them is considerably higher than that of the other. As a result, it has been made possible to isolate the optically active cyclopentenone ethers in a good yield with a high purity by a simple operation.

According to the present invention, the 2-substituted or unsubstituted-4-hydroxy-2-cyclopentenone of the formula:

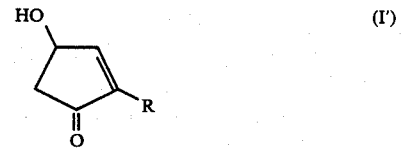
(I')

wherein R is as defined above and a lactone chosen from (1R,5S)-6,6-dimethyl-4-hydroxy-3-oxabicyclo[3.1.0]hexan-2-one or (1S,5R)-6,6-dimethyl-4-hydroxy-3-oxabicyclo[3.1.0]hexan-2-one are reacted in a molar ratio of 1.5 - 2:1 in the presence of p-toluenesulfonic acid or benzenesulfonic acid in the coexistence of an organic solvent under elimination of water as an azeotropic mixture with the organic solvent to obtain a reaction mixture comprising (1R,5S)-6,6-dimethyl-3-oxa-4(R)-[1(R)-4-oxo-2-substituted or unsubstituted-2-cyclopentenyloxy]bicyclo[3.1.0]hexan-2-one or (1S,5R)-6,6-dimethyl-3-oxa-4(S)-[1(S)-4-oxo-2-substituted or unsubstituted-2-cyclopentenyloxy]bicyclo[3.1.0]hexan-2-one of the formula:

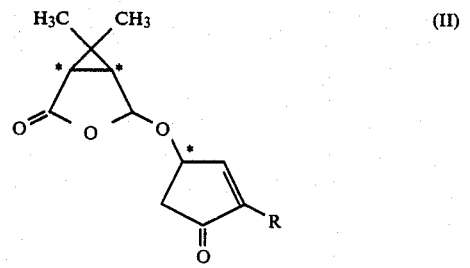
(II)

wherein R is as defined above, wherein one of the isomers is contained in a considerably larger amount than the other isomer, the isomer having the larger content is separated from the reaction mixture, and the separated isomer is hydrolyzed to give the optically active 2-substituted or unsubstituted-4-hydroxy-2-cyclopentenone (I).

The above process of the invention will be hereinafter explained in more details.

First, the 2-substituted or unsubstituted-4-hydroxy-2-cyclopentenone (I') is reacted with the lactone in a molar proportion of 1.5–2:1. It is essential that the reactants are used in said molar proportion, because only in such case is one of the optically active isomers obtained as a reaction product in an amount significantly larger than that of the other isomer, and the subsequent separation is accomplished advantageously.

For instance, in the reaction between 4-hydroxy-2-cyclopentenone (I': R=H) and (1R,5S)-6,6-dimethyl-4-hydroxy-3-oxabicyclo[3.1.0]hexan-2-one, the proportion of (1R,5S)-6,6-dimethyl-3-oxa-4(R)-[1(R)-4-oxo-2-cyclopentenyloxy]bicyclo[3.1.0]hexan-2-one (hereinafter referred to as [I-a]) and (1R,5S)-6,6-dimethyl-3-oxa-4(R)-[1(S)-4-oxo-2-cyclopentenyloxy]bicyclo[3.1.0]hexan-2-one (hereinafter referred to as [I-b]) as produced (i.e. the [I-a]/[I-b] ratio) is significantly larger than 1 only when the molar ratio of said reactants is from 1.5 to 2 (cf. FIG. 1 of the accompanying drawing). The similar tendency to the above is also seen in the case wherein 2-allyl-4-hydroxy-2-cyclopentenone (I': R=allyl) is reacted with said lactone to give a reaction mixture comprising (1R,5S)-6,6-dimethyl-3-oxa-4(R)-[1(R)-4-oxo-3-allyl-2-cyclopentenyloxy]bicyclo[3.1.0]hexan-2-one (hereinafter referred to as [II-a]) and (1R,5S)-6,6-dimethyl-3-oxa-4(R)-[1(S)-4-oxo-3-allyl-2-cyclopentenyloxy]bicyclo[3.1.0]hexan-2-one (hereinafter referred to as [II-b]) and in the case wherein 2-propargyl-4-hydroxy-2-cyclopentenone (I': R=propargyl) is reacted with said lactone to give a reaction mixture comprising (1R,5S)-6,6-dimethyl-3-oxa-4(R)-[1(R)-4-oxo-3-propargyl-2-cyclopentenyloxy]bicyclo[3.1.0]hexan-2-one (hereinafter referred to as [III-a]) and (1R,5S)-6,6-dimethyl-3-oxa-4(R)-[1(S)-4-oxo-3-propargyl-2-cyclopentenyloxy]bicyclo[3.1.0]-hexan-2-one (hereinafter referred to as [III-b]). Namely, the [III-a]/[III-b] ratio as well as the [II-a]/[II-b] ratio are significantly larger than 1, when the molar ratio of said reactants is within the range as defined above.

Further, in the reaction between 4-hydroxy-2-cyclopentenone (I': R =H) and (1S,5R)-6,6-dimethyl-4-hydroxy-3-oxabicyclo[3.1.0]hexan-2-one, there is obtained a reaction mixture comprising (1S,5R)-6,6-dimethyl-3-oxa-4(S)-[1(S)-4-oxo-2-cyclopentenyloxy]-bicyclo[3.1.0]hexan-2-one (hereinafter referred to as [I-d]) and (1S,5R)-6,6-dimethyl-3-oxa-4(S)-[1(R)-4-oxo-2-cyclopentenyloxy]bicyclo[3.1.0]hexan-2-one (hereinafter referred to as [I-c]), the [I-d]/[I-c] ratio being significantly larger than 1. Likewise, the reaction between 2-allyl-4-hydroxy-2-cyclopentenone (I': R=allyl) and said lactone affords a reaction mixture comprising (1S,5R)-6,6-dimethyl-3-oxa-4(S)-[1(S)-4-oxo-3-allyl-2-cyclopentenyloxy]bicyclo[3.1.0]-hexan-2-one (hereinafter referred to as [II-d]) and (1S,5R)-6,6-dimethyl-3-oxa-4(S)-[1(R)-4-oxo-3-allyl-2-cyclopentenyloxy]bicyclo[3.1.0]hexan-2-one (hereinafter referred to as [II-c]), the [II-d]/[II-c] ratio being significantly larger than 1. Also, the reaction between 2-propargyl-4-hydroxy-2-cyclopentenone (I': R=propargyl) and said lactone gives a reaction mixture comprising (1S,5R)-6,6-dimethyl-3-oxa-4(S)-[1(S)-4-oxo-3-propargyl-2-cyclopentenyloxy]bicyclo[3.1.0]hexan-2-one (hereinafter referred to as [III-d]) and (1S,5R)-6,6-dimethyl-3-oxa-4(S)-[1(R)-4-oxo-3-propargyl-2-cyclopentenyloxy]-bicyclo[3.1.0]hexan-2-one (hereinafter referred to as [III-c]), the [III-d]/[III-c] ratio being singificantly larger than 1.

As the catalyst, there may be used p-toluenesulfonic acid or benzenesulfonic acid. Their pyridine salts are not favorable, because the favorable optically active isomer ratio is not obtained. The amount of the catalyst to be used may be usually from 0.005 to 0.5 equivalent, preferably from 0.01 to 0.2 equivalent, to the lactone.

As the organic solvent, there may be used any one which can form an azeotropic mixture with water. Specific examples are benzene, toluene, etc. Since the reaction is a kind of condensation, it is desirable to eliminate the water as during the reaction from the reaction system, whereby the reaction is promoted. The azeotropic mixture removed from the reaction system may be cooled, followed by separation of water; the resultant solvent may be returned to the reaction system.

The reaction temperature may be such a temperature as can form an azeotropic mixture between the organic solvent and the by-produced water. It is usually from 50 to 120° C., preferably from 60° C. to 115° C. The reaction time depends upon the other reaction conditions, and any particular limitation is not present. In general, it may be from 2 to 7 hours.

The optically active isomer having a higher content is recovered from the reaction mixture. The difference between the amount of the optically active isomer having a higher content and of the amount of the optically active isomer having a lower content in the reaction mixture is so significant that separation of the former from the reaction mixture can be readily accomplished by a conventional separation procedure such as column chromatography or crystallization.

For column chromatography, there may be used such a carrier as silica gel or alumina, usually in an amount of about 4 to 70 parts by weight to one part by weight of the cyclopentenone ethers (II). As the eluting solvent, there may be used any ordinary solvent such as toluene, ethyl acetate, hexane, petroleum ether, isopropylether or dichloromethane. Their mixtures are also usable. By such separation procedure, the optically active cyclopentenone ether can be recovered efficiently with a high optical purity.

In case of 4-hydroxy-2-cyclopentenone (I': R=H), the [I-a]/[I-b] ratio or the [I-d]/[I-c] ratio is particularly high so that separation of the optically active cyclopentenone ether [I-a] or [I-d] may be accomplished preferably by crystallization. For crystallization, there may be used any ordinary solvent such as toluene, ethyl acetate, hexane or isopropyl ether. Their mixtures are also usable. The crystallization may be carried out by a per se conventional procedure, for instance, by the aid of the seed crystals. Any particular limitation is not present on the amount of the solvent, and it may be usually from 0.3 to 10 parts by weight to one part by weight of the cyclopentenone ethers. The temperature for crystallization is not limitative and may be appropriately decided on the kind and amount of the solvent as used. In usual, it is within a range of −20° to 90° C.

When desired, the once recovered optically active cyclopentenone ether (II) may be further purified, for instance, by recrystallization using the solvent as exemplified above.

The optically active cyclopentenone ether (II) thus obtained is then subjected to hydrolysis. The hydrolysis may be effected under a neutral condition in view of the stability of the optically active 2-substituted or unsubstituted-4-hydroxy-2-cyclopentenone (I) as ultimately produced. For instance, the optically active cyclopentenone ether (II) may be heated usually in water of about 2 to 20 folds in weight. While any water-misciable organic solvent (e.g. dioxane, tetrahydrofuran, dimethylformamide, dimethylsulfoxide) may coexist, its coexistence is usually not favorable for post-treatment or further purification. The heating temperature may be normally from 50° to 100° C., preferably from 60° to 100° C. No particular limitation is present on the heating time.

Separation of the optically active 2-substituted or unsubstituted-4-hydroxy-2-cyclopentenone (I) from the reaction mixture after hydrolysis may be carried out, for instance, by allowing the reaction mixture to cool, if necessary, with previous concentration. The precipitated lactone is eliminated by filtration, and the filtrate may be concentrated to recover the optically active 2-substituted or unsubstituted-4-hydroxy-2-cyclopentenone (I), which may be further purified by chromatography, distillation or the like if desired.

As understood from the above, the process of this invention can afford industrially the optically active 2-substituted or unsubstituted-4-hydroxy-2-cyclopentenone (I) in a good yield with a high purity by a simple operation.

Practical and presently preferred embodiments of the invention are illustratively shown in the following examples, wherein part(s) and % are by weight unless otherwise indicated.

EXAMPLE 1

Into a four-necked flask equipped with a stirrer, a thermometer and an azeotropic distillator, 4-hydroxy-2cyclopentenone (19.62 g; 200 mmol), (1R,5S)-6,6-dimethyl-4-hydroxy-3-oxabicyclo[3.1.0]hexane-2-one (16.76 g; 118 mmol), p-toluenesulfonic acid (0.44 g) and benzene (160 ml) were charged and heated under reflux. The resultant mixture was allowed to react for 4 hours, during which by-produced water was azeotropically distilled out from the reaction system. After completion of the reaction, water (80 ml) was added to the reaction mixture. The organic layer was separated, washed with a 3 % aqueous sodium carbonate solution (60 ml) and water (70 ml) in order and concentrated under reduced pressure to give a mixture (25.02 g) of (1R,5S)-6,6-dimethyl-3-oxa-4(R)-[1(R)-4-oxo-2-cyclopentenyloxy]-bicyclo[3.1.0]hexan-2-one [I-a] and (1R,5S)-6,6-dimethyl-3-oxa-4(R)-[1(S)-4-oxo-2-cyclopentenyloxy]bicyclo[3.1.0]hexan2-one [I-b], the [I-a]/[I-b] ratio being 1.82.

The thus obtained mixture (15 g) was dissolved in ethyl acetate (10 ml), to which hexane (6 ml) was added at 50° C. The resultant mixture was gradually cooled, and (1R,5S)-6,6-dimethyl-3-oxa-4(R)-[1(R)-4-oxo-2-cyclopentenyloxy]bicyclo[3.1.0]hexan-2-one [I-a] (10 mg) as the seed crystal was added thereto at 25° C. The mixture was further cooled, kept at 0° C. for 8 hours and subjected to filtration under cooling to give [I-a] (3.52 g) as crystals. $[\alpha]_D^{20}$ −44.9° (c=1, methanol). M.P., 90° C.

To [I-a] (3 g), water (10 ml) was added, and the resultant mixture was heated at 75° C. for 3 hours. The reaction mixture was concentrated under reduced pressure to remove water (4 ml), followed by cooling at 0° C. and allowing to stand for 3 hours. The precipitated crystals (i.e. the lactone) were collected by filtration, and the filtrate was concentrated. The residue was purified by column chromatography to give 1.25 g of 4(R)-hydroxy-2-cyclopentenone. $[\alpha]_D^{20}$+96° (c=1, methanol).

EXAMPLE 2

Into the same flask as used in Example 1, 4-hydroxy-2-cyclopentenone (23.15 g; 236 mmol), (1R,5S)6,6-dimethyl-4-hydroxy-3-oxabicyclo[3.1.0]hexan-2-one (16.76 g; 118 mmol), p-toluenesulfonic acid (0.44 g) and toluene (160 ml) were charged and heated under reflux. The resultant mixture was allowed to react for 4 hours, during which by-produced water was azeotropically distilled out from the reaction system. After completion of the reaction, the same work-up as in Example 1 gave a mixture (25.32 g) of (1R,5S)-6,6-dimethyl-3-oxa-4(R)-[1(R)-4-oxo-2-cyclopentenyloxy]bicyclo[3.1.0]hexan-2-one [I-a] and (1R,5S)-6,6-di-methyl-3-oxa-4(R)-[1(S)-4-oxo-2-cyclopentenyloxy]bicyclo-[ 3.1.0]hexan-2-one [I-b], the [I-a]/[I-b] ratio being 1.72.

The thus obtained mixture (15 g) was subjected to column chromatography using a mixture of ethyl acetate and hexane (4:6) as an eluent, followed by recrystallization from a mixture of isopropyl ether and ethyl acetate (10:1) to give 8.66 g of [I-a]. $[\alpha]_D^{20}$−45.2° (c=1, methanol). M.P., 90°–91° C.

To [I-a] (3 g), water (10 ml) was added, and the resultant mixture was heated at 70° C. for 4 hours. The reaction mixture was subjected to the same work-up and purification as in Example 1 to give 1.24 g of 4(R)-hydroxy-2-cyclopentenone. $[\alpha]_D^{20}$+97.5° (c=1, ethanol). $n_D^{20}$ 20 1.5035.

To [I-a] (3 g), water (6 ml) and dioxane (6 ml) were added, and the resultant mixture was heated at 75° C. for 4 hours. The reaction mixture was concentrated under reduced pressure, water (6 ml) was added thereto, and the resultant mixture was cooled to 0° C. The precipitated crystals (i.e. the lactone) were collected by filtration, and the filtrate was concentrated. The residue was purified by column chromatography to give 1.22 g of 4(R)-hydroxy-2-cyclopentenone. $[\alpha]_D^{20}$+97.4° (c=1, ethanol). $n_D^{20}$ 1.5033.

EXAMPLE 3

In the same manner as in Example 1 but using benzenesulfonic acid (0.4 g) instead of p-toluenesulfonic acid, the reaction was carried out to give a mixture (25.08 g) of (1R,5S)-6,6-dimethyl-3-oxa-4(R)-[1(R)-4-oxo-2-cyclopentenyloxy]bicyclo[3.1.0]hexan-2-one [I-a] and (1R,5S)- 6,6-dimethyl-3-oxa-4(R)-[1(S)-4-oxo-2-cyclopentenyloxy]bicyclo[3.1.0]hexan-2-one [I-b], the [I-a]/[I-b] ratio being 1.78.

The thus obtained mixture (15 g) was dissolved in ethyl acetate (10 ml), to which hexane (12 ml) was added at 50° C. The resultant mixture was gradually cooled, and (1R,5S)-6,6-dimethyl-3-oxa-4(R)-[1(R)-4-oxo-2-cyclopentenyloxy]bicyclo[3.1.0]hexan-2-one [I-a] (10 mg) as the seed crystals was added thereto at 25° C. The mixture was further cooled, kept at 10° C. for 5 hours and subjected to filtration to give [I-a] (3.06 g) as crystals.

To [I-a] (3 g), water (10 ml) was added, and the resultant mixture was heated at 80° C. for 1 hour. The same work-up and purification as in Example 1 gave 1.22 g of 4(R)-hydroxy-2-cyclopentenone. $[\alpha]_D^{20}+96.4°$ (c=1, ethanol).

EXAMPLE 4

Into the same flask as used in Example 1, 2-allyl-4-hydroxy-2-cyclopentenone (24.42 g; 0.177 mol), (1R,5S)-6,6-dimethyl-4-hydroxy-3-oxabicyclo[3.1.0-]hexan-2-one (16.76 g; 0.118 mol), p-toluenesulfonic acid (0.44 g) and benzene (150 ml) were charged and heated under reflux. The resultant mixture was allowed to react for 4 hours, during which by-produced water was azeotropically distilled out from the reaction system. After completion of the reaction, water (80 ml) was added to the reaction mixture. The organic layer was separated, washed with a 3 % aqueous sodium carbonate solution (60 ml) and water (70 ml) in order and concentrated under reduced pressure to give a mixture (32.1 g) of (1R,5S)-6,6-dimethyl-3-oxa-4(R)-[1(R)-4-oxo-3-allyl-2-cyclopentenyloxy]bicyclo[3.1.0-]hexan-2-one [II-a]and (1R,5S)-6,6-dimethyl-3-oxa-4(R)-[1(S)-4-oxo-3-allyl-2-cyclopentenyloxy]bicyclo[3.1.0]hexan-2-one [II-b], the [II-a] [II-b] ratio being 1.63.

The thus obtained mixture was purified by silica gel column chromatography using a mixture of dichloromethane and ethyl acetate (100:1) as an eluent to give 18.42 g of [II-a]. $[\alpha]_D^{20}-55.9°$ (c=1, ethanol).

Then, a mixture of [II-a] (3 g) and water (10 ml) was allowed to react while heating at 75° C. for 3 hours. The same work-up and purification as in Example 1 gave 1.52 g of 4(R)-hydroxy-2-cyclopentenone. $[\alpha]_D^{20}+19.3°$ (c=1, chloroform). $n_D^{20}$ 1.5044.

EXAMPLE 5

Into the same flask as used in Example 1, 4-hydroxy-2-propargyl-2-cyclopentenone (21.76 g; 0.16 mol), (1R,5S)-6,6-dimethyl-4-hydroxy-3-oxabicyclo[3.1.0-]hexan-2-one (14.2 g; 0.1 mol), benzenesulfonic acid (0.3 g) and toluene (100 ml) were charged and heated under reflux in vacuo. The resultant mixture was allowed to react at 80° to 85° C. for 4 hours, during which by-produced water was azeotropically distilled out from the reaction system. After completion of the reaction, water (60 ml) was added to the reaction mixture. The organic layer was separated, washed with a 3 % aqueous sodium hydrogen carbonate solution (50 ml) and water (60 ml) in order and concentrated under reduced pressure to give a mixture (25.74 g) of (1R,5S)6,6-dimethyl-3-oxa-4(R)-[1(R)-4-oxo-3-propargyl-2-cyclopentenyloxy]bicyclo[3.1.0]hexan-2-one [III-a]and (1R,5S)6,6-dimethyl-3-oxa-4(R)-[1(S)-4-oxo-3-propargyl-2-cyclopentenyloxy]bicyclo[3.1.0]hexan-2-one [III-b], the [III-a]/[III-b] ratio being 1.6.

The thus obtained mixture was purified by silica gel column chromatography using a mixture of dichloromethane and ethyl acetate (100:2) as an eluent to give 15.22 g of [III-a]. $[\alpha]_D^{20}-77.1°$ (c=1, ethanol). $n_D^{20}$ 1.5206.

A mixture of [III-a] (5 g) and water (15 ml) was allowed to react while heating at 75° to 80° C. for 3 hours. The same work-up and purification as in Example 1 gave 2.49 g of 4(R)-hydroxy-2-propargyl-2-cyclopentenone. $[\alpha]_D^{20}+10.3°$ (c=1, chloroform). $n_D^{20}$ 1.5187.

EXAMPLE 6

In the same manner as in Example 5 but using (1S,5R)-6,6-dimethyl-4-hydroxy-3-oxabicyclo[3.1.0-]hexan2-one instead of (1R,5S)-6,6-dimethyl-4-hydroxy-3-oxabicyclo[3.1.0]hexan-2-one, the reaction was carried out to give a mixture (25.62 g) of (1S,5R)-6,6-dimethyl-3-oxa-4(S)-[1(S)-4-oxo-3-propargyl-2-cyclopentenyloxy]bicyclo[3.1.0]-hexan-2-one [III-d]and (1S,5R)-6,6-dimethyl-3-oxa-4(S)-[1(R)-4-oxo-3-propargyl-2-cyclopentenyloxy]bicyclo[3.1.0]-hexan-2-one [III-c], the [III-d]/[III-c] ratio being 1.61.

The thus obtained mixture was purified by column chromatography to give 15.16 g of [III-d]. $[\alpha]_D^{20}+76.9°$ (c=1, ethanol). $n_D^{20}$ 1.5199.

Then, a mixture of [III-d] (5 g) and water (15 ml) was allowed to react while heating at 75° to 80° C. for 3 hours. The same work-up and purification as in Example 1 gave 2.51 g of 4(S)-hydroxy-2-propargyl-2-cyclopentenone. $[\alpha]_D^{20}-10.2°$ (c=1, chloroform). $n_D^{20}$ 1.5184.

EXAMPLE 7

In the same manner as in Example 1 but using (1S,5R)-6,6-dimethyl-4-hydroxy-3-oxabicyclo[3.1.0-]hexan-2-one instead of (1R,5S)-6,6-dimethyl-4-hydroxy-3-oxabicyclo[3.1.0]hexan-2-one, the reaction was carried out to give a mixture (25.26 g) of (1S,5R)-6,6-dimethyl-3-oxa-4(S)-[1(S)-4-oxo-2-cyclopentenyloxy]bicyclo[3.1.0]hexan-2-one [I-d] and (1S,5R)-6,6-dimethyl-3-oxa-4(S)-[1(R)-4-oxo-2-cyclopentenyloxy]bicyclo[3.1.0]hexan-2-one [I-c], the [I-d]/[I-c] ratio being 1.79.

The thus obtained mixture (10 g) was purified by silica gel column chromatography using a mixture of ethyl acetate and hexane (4:6) as an eluent to give 5.90 g of [I-d]. $[\alpha]_D^{20}+44.8°$ (c=1, methanol). M.P., 88°-90° C.

Then, a mixture of [I-d] (3 g) and water (10 ml) was allowed to react while heating at 75° C. for 3 hours. The same work-up and purification as in Example 1 gave 1.25 g of 4(S)-hydroxy-2-cyclopentenone. $[\alpha]_D^{20}-96.8°$ (c=1, ethanol). $n_D^{20}$ 1.5039.

The above obtained mixture (15 g) was dissolved in ethyl acetate (10 ml), and hexane (6 ml) was added thereto at 50° C. The resultant mixture was gradually cooled and kept at 0° C., followed by filtration under cooling to give [I-d] (3.51 g) as crystals. $[\alpha]_D^{20}+45.0°$ (c=1, methanol). M.P., 90°-91° C.

The thus obtained [I-d] (3 g) was subjected to hydrolysis and purification to give 1.26 g of 4(S)-hydroxy-2-cyclopentenone. $[\alpha]_D^{20}-97.3°$ (c=1, ethanol). $n_D^{20}$ 1.5038.

What is claimed is:

1. A process for preparing an optically active 2-substituted or unsubstituted-4-hydroxy-2-cyclopentenone of the formula:

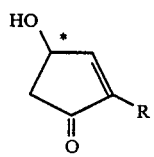

wherein R is a hydrogen atom, an allyl group or a propargyl group, which comprises reacting the corresponding 2-substituted or unsubstituted-4-hydroxy-2-cyclopentenone of the formula:

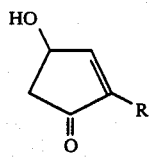

wherein R is defined above with a lactone chosen from (1R,5S)-6,6-dimethyl-4-hydroxy-3-oxabicyclo[3.1.0-]hexan-2one or (1S,5R)-6,6-dimethyl-4-hydroxy-3-oxabicyclo[3.1.0]-hexan-2-one in a molar ratio of 1.5 - 2:1 in the presence of p-toluenesulfonic acid or benzenesulfonic acid in the coexistence of an organic solvent under elimination of water as an azeotropic mixture with the organic solvent to obtain a reaction mixture comprising (1R,5S)-6,6-dimethyl-3-oxa 4(R)-[1(R)-4-oxo-2-substituted or unsubstituted-2-cyclopentenyloxy]bicyclo[3.1.0]hexan-2-one or (1S,5R)-6,6-dimethyl-3-oxa-4(S)-[1(S)-4-oxo-2-substituted or unsubstituted-2-cyclopentenyloxy]bicyclo[3.1.0]hexan-2-one of the formula:

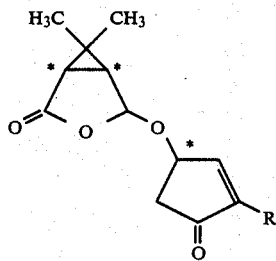

wherein R is as defined above, wherein one of the isomers is contained in a considerably larger amount than the other isomer, separating the isomer having the larger content from the reaction mixture and hydrolyzing the separated isomer to give the optically active 2-substituted or unsubstituted-4-hydroxy-2-cyclopentenone.

2. The process according to claim 1, wherein the 2-substituted or unsubstituted-4-hydroxy-2-cyclopentenone is 4-hydroxy-2-cyclopentenone.

3. The process according to claim 1, wherein p-toluenesulfonic acid or benzenesulfonic acid is used in an amount of 0.005 to 0.5 equivalent to the lactone.

4. The process according to claim 3, wherein p-toluenesulfonic acid or benzenesulfonic acid is used in an amount of 0.01 to 0.2 equivalent to the lactone.

5. The process according to claim 1, wherein the temperature at which water is eliminated as the azeotropic mixture is from 50° to 120° C.

6. The process according to claim 5, wherein the temperature at which water is eliminated as the azeotropic mixture is from 60° to 115° C.

7. The process according to claim 1, wherein the organic solvent is toluene or benzene.

8. The process according to claim 1, wherein the separation is carried out by crystallization.

9. The process according to claim 1, wherein the separation is carried out by column chromatography.

10. The process according to claim 1, wherein the hydrolysis is carried out in an aqueous medium.

11. The process according to claim 1, wherein said molar ratio is 1.6–2:1.

12. The process according to claim 1, wherein said molar ratio is 1.7–2:1.

13. The process according to claim 1, wherein one of the isomers is obtained in a molar ratio amount of 1.6–1.82:1 relative to the other isomer.

* * * * *